US008712509B2

(12) United States Patent
Lee et al.

(10) Patent No.: US 8,712,509 B2
(45) Date of Patent: Apr. 29, 2014

(54) VIRTUAL PHYSICIAN ACUTE MYOCARDIAL INFARCTION DETECTION SYSTEM AND METHOD

(75) Inventors: Brian Bruce Lee, Golden Valley, MN (US); Eric John Wengreen, Blaine, MN (US); Zhendong Song, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1247 days.

(21) Appl. No.: 12/180,268

(22) Filed: Jul. 25, 2008

(65) Prior Publication Data
US 2010/0022902 A1 Jan. 28, 2010

(51) Int. Cl.
A61B 5/0452 (2006.01)
A61B 5/00 (2006.01)

(52) U.S. Cl.
CPC .................................. *A61B 5/0002* (2013.01)
USPC ........... 600/513; 600/301; 600/509; 600/516; 607/30; 607/32; 607/59; 607/60; 607/62

(58) Field of Classification Search
CPC .................................................. A61B 5/0002
USPC ........ 600/509, 513, 516, 301; 607/30, 32, 59, 607/60, 62
See application file for complete search history.

(56) References Cited

U.S. PATENT DOCUMENTS

| 5,722,999 | A | | 3/1998 | Snell | |
|---|---|---|---|---|---|
| 6,045,513 | A | | 4/2000 | Stone et al. | |
| 6,101,478 | A | | 8/2000 | Brown | |
| 6,128,526 | A | * | 10/2000 | Stadler et al. | 600/517 |
| 6,206,829 | B1 | | 3/2001 | Hiff | |
| 6,233,486 | B1 | | 5/2001 | Ekwall et al. | |
| 6,937,899 | B2 | | 8/2005 | Sheldon et al. | |
| 7,066,891 | B2 | | 6/2006 | Stadler et al. | |
| 7,181,268 | B2 | | 2/2007 | Sheldon et al. | |
| 7,207,945 | B2 | * | 4/2007 | Bardy | 600/529 |
| 7,899,545 | B2 | * | 3/2011 | John | 607/60 |
| 2001/0051764 | A1 | | 12/2001 | Bardy | |
| 2004/0122297 | A1 | * | 6/2004 | Stahmann et al. | 600/300 |
| 2004/0215092 | A1 | | 10/2004 | Fischell et al. | |
| 2005/0033121 | A1 | * | 2/2005 | Modrovich | 600/300 |

(Continued)

FOREIGN PATENT DOCUMENTS

EP 1072994 A2 1/2001

OTHER PUBLICATIONS

PCT International Search Report (PCT/US2009/051220).

*Primary Examiner* — Christopher D Koharski
*Assistant Examiner* — Natasha Patel
(74) *Attorney, Agent, or Firm* — Michael J. Ostrom

(57) ABSTRACT

A system and method for virtually detecting a medical condition, such as acute myocardial infarction (AMI), in a patient using holistic diagnostic procedures implemented in medical devices. Physiological parameters in a patient are monitored in an implantable medical device (IMD) to detect deviations from desired characteristics. When severe physiological parameter deviations exist indicating with a desired certainty that the patient is experiencing a medical condition (e.g., AMI), an alert is generated. If only minor deviations from the desired characteristics exist, additional holistic diagnostic procedures are performed virtually for diagnosing whether the patient is likely to be experiencing the medical condition, such as querying the patient through an external device regarding symptoms the patient is experiencing and analyzing the patient's responses to the questions to determine whether the patient is experiencing the medical condition. When diagnosis is still unclear, additional holistic diagnostic procedures can be performed virtually until diagnosis is certain.

16 Claims, 7 Drawing Sheets

(56) References Cited

U.S. PATENT DOCUMENTS

| | | | |
|---|---|---|---|
| 2007/0021979 A1* | 1/2007 | Cosentino et al. | 705/2 |
| 2007/0250127 A1 | 10/2007 | Stylos et al. | |
| 2009/0048503 A1* | 2/2009 | Dalal et al. | 600/365 |
| 2010/0010361 A1* | 1/2010 | Boute et al. | 600/519 |

* cited by examiner

VIRTUAL PHYSICIAN ACUTE MYOCARDIAL INFARCTION DETECTION SYSTEM AND METHOD

TECHNICAL FIELD

This disclosure relates generally to medical devices and implantable medical devices and, more particularly, to a system and method for detecting acute myocardial infarction using such devices.

BACKGROUND

Coronary heart disease (CHD) is the single leading cause of death in America. Many studies demonstrate the critical importance of shortening the time from acute myocardial infarction (AMI) symptom onset to treatment. Although differing opinions exist regarding time-to-treatment guidelines, many physicians suggest the time-to-treatment goal should be one hour. Meeting this goal is often not practical due to the fact much of this "golden hour" is commonly consumed by patients wondering if the symptoms they are experiencing are related to a heart attack or simply another non-life threatening physiological condition (e.g., heartburn, sore muscles, etc.). Patients usually rush to the hospital when they suffer extremely painful heart attacks, but many heart attacks are only accompanied by relatively minor discomfort that, while obviously present, can be easily confused with non-threatening conditions. By the time the patient decides to seek medical help, much or all of the "golden hour" has often passed.

Historically, acute myocardial infarction (AMI) has been diagnosed by a physician when the patient is experiencing ischemic chest pain typically associated with AMI and electrogram (EGM)/electrocardiogram (ECG) signals have characteristics typically associated with AMI (e.g., ST segment elevation and pathological Q-waves). It has been difficult for prior medical devices, either implantable or external, to detect AMI with satisfactory levels of sensitivity and specificity based on measured EGM/ECG signals. For example, ST segment deviations may not necessarily be due to AMI but could be due various other artifacts. This difficulty in detection has led to the late recognition of AMI and action by the patient in seeking assistance, thereby leading to long delays until therapies are delivered to the patient.

SUMMARY

In one or more embodiments, a system and method are provided for virtually detecting a medical condition in a patient using holistic diagnostic procedures that typically require physician assistance in order to complete. The system and method are particularly well-suited for detecting acute myocardial infarction (AMI) accurately and rapidly after the onset of AMI.

In one or more embodiments, the system and method include sensing at least one physiological signal in a patient's body received in an implantable medical device and monitoring a corresponding physiological parameter from each sensed signal to detect deviations in the monitored physiological parameter from normal, desired or expected characteristics. When physiological parameter deviations exist, it is determined whether sufficient deviations are present in the monitored physiological parameter that indicate with a desired level of certainty that the patient is experiencing a certain medical condition (e.g., AMI) and generating an alert when the desired level of certainty that the patient is experiencing the medical condition exists. In one or more embodiments, the alert may include a patient, physician, caregiver or emergency response (ER) team notification of the detected medical condition, which may further include the transfer of data from the implantable medical device via a communication link or network.

In one or more embodiments, if minor deviations from desired or expected characteristics exist in the monitored physiological parameter but are not severe enough to indicate with a desired level of certainty that the patient is experiencing a certain medical condition, additional holistic diagnostic procedures are performed for diagnosing whether the patient is likely to be experiencing the medical condition. In one or more embodiments, the additional holistic diagnostic procedures include querying the patient with questions relating to any symptoms the patient may be experiencing. The patient's responses to the symptom-related questions are collected and analyzed further in view of the detected minor physiological parameter deviations to holistically diagnose whether the patient is experiencing a certain medical condition. An alert may be generated when the analysis of the patient's responses to the symptom-related questions indicates with a desired probability that the patient is experiencing the medical condition. In one or more embodiments, the various diagnostic procedures may be initiated by the request of the patient, possibly in response to certain symptoms the patient is experiencing. In one or more embodiments, if the ultimate diagnosis is negative, the patient is notified of the negative diagnosis. The notification of the negative diagnosis (e.g., notification that the patient is not experiencing a certain medical condition) adds to the effective result of the holistic diagnosis that is performed virtually.

In one or more embodiments, if the patient does not respond within a certain period of time, this lack of responsiveness may be used as an additional factor in determining whether the patient is experiencing a medical condition (i.e., the lack of responsiveness may indicate that the patient is unable to respond based upon the medical condition). In one or more embodiments, additional factors may be analyzed and utilized in determining whether the patient's lack of responsiveness should be given a higher or lower weight when determining whether the patient is experiencing the medical condition, where such factors may include the time of day, the degree of patient activity, or the factors in the patient's surrounding environment. For example, the patient's lack of responsiveness may be due to the patient being asleep (e.g., by sensing the time of day and/or using activity level measurements from accelerometers), due to the patient being involved in a distracting activity (e.g., by using activity level measurements from accelerometers), due to the patient not being able to sense the prompts to the symptom-related questions (e.g., by sensing acoustic levels in the patient's environment that may prevent the patient from hearing audible alerts), or due to a loss in the communication link to the patient. In some embodiments, the position of the patient can be sensed and this position can be used to assist in determining whether the patient is experiencing the medical condition.

In one or more embodiments, an external device accessible by the patient is used to query the patient with the symptom-related questions. In some embodiments, the external device may include a portable device (e.g., a mobile phone, PDA, mobile dedicated processing unit, etc.) or a device installed in the patient's home (e.g., an in-home patient monitoring system, personal computer, etc.). Upon detection of minor physiological parameter deviations, the implantable medical device transmits an instruction or command to the external device to prompt the patient to respond to the symptom-related questions. The external device may further include a notification mechanism (e.g., an audible or visual or tactile notification) in order to prompt the patient to respond to the query.

In one or more embodiments, when the responses to the patient query fail to indicate with the desired probability that the patient is experiencing the medical condition, the external device is further configured for causing at least one additional physiological parameter diagnostic test to be performed to determine whether the patient is experiencing the medical condition. In one or more embodiments, the additional physiological parameter diagnostic tests can alternatively be performed prior to, at the same time, and/or in place of the symptom-related query to the patient. In some embodiments, the additional physiological parameter diagnostic tests are performed automatically by instructing the implantable medical device or another internal or external device to obtain measurements of another physiological parameter. In some embodiments, the patient is instructed to perform the additional physiological parameter diagnostic tests and enter the results of such tests into the external device. An alert may be generated when the analysis of the additional physiological parameter diagnostic tests indicates with a desired probability that the patient is experiencing the medical condition. In this manner, a medical condition in a patient can be rapidly detected in a virtual environment using holistic diagnostic procedures near a point in time of the onset of the medical condition without requiring a physician interaction.

The system for virtual detection of a medical condition may be implemented in an implantable or external medical device or a combination distributed medical devices arranged with respect to a patient to monitor at least one physical parameter. The system includes one or more physiological sensors coupled to a signal processing controller in the medical device for monitoring physiological parameters. The system further includes processing circuitry for detecting deviations in the monitored physiological parameter from desired or expected characteristics, generating alerts and prompting an external patient-accessible device to query the patient with symptom-related questions. The external device further includes processing circuitry for receiving the patient's responses to the query, and may further include components for generating an alert if a predefined level of certainty has been reached indicating the detection of the medical condition based on the patient's responses taken alone or in combination of the monitored physiological parameters. The external device further includes processing circuitry for initiating additional physiological parameter diagnostic tests to be performed when the responses to the patient query fail to indicate with the desired probability that the patient is experiencing the medical condition. At least one of the external device and the implantable medical device includes processing circuitry for analyzing the results of the additional physiological parameter diagnostic tests and generating alerts when a medical condition is detected. The processing circuitry may include a processor or controller for executing instructions in a software program stored on at least one of the medical and external devices.

In one or more embodiments, the specific medical condition to be detected includes acute myocardial infarction, such that an electrogram (EGM) signal received in the implantable medical device is monitored for ST segment deviations. Acute myocardial infarction may then be virtually diagnosed when it is determined that sufficient ST segment deviations exist in the monitored EGM signal that indicate with a desired level of certainty that the patient is experiencing acute myocardial infarction. When only minor ST segment deviations are present in the monitored EGM signal that potentially indicate that the patient is experiencing acute myocardial infarction without reaching with the desired level of certainty that the patient is indeed experiencing acute myocardial infarction, additional holistic diagnostic procedures may then be performed for virtually diagnosing whether the patient is experiencing acute myocardial infarction. Such additional holistic diagnostic procedures may include querying the patient regarding symptoms the patient is experiencing, performing a heart sounds diagnostic test, performing a biomarker test or other relevant tests that can be performed until it is determined holistically with sufficient certainty whether the patient is experiencing acute myocardial infarction. In some embodiments, the system may ask the patient to get into a particular posture or position, to take certain actions (e.g., to be quiet, stop moving, etc.) to assume any other measures that may improve the quality of the sensed signal that are used to determine whether the patient is experiencing the medical condition

DRAWINGS

The above-mentioned features and objects of the present disclosure will become more apparent with reference to the following description taken in conjunction with the accompanying drawings wherein like reference numerals denote like elements and in which.

DETAILED DESCRIPTION

Figure 1:
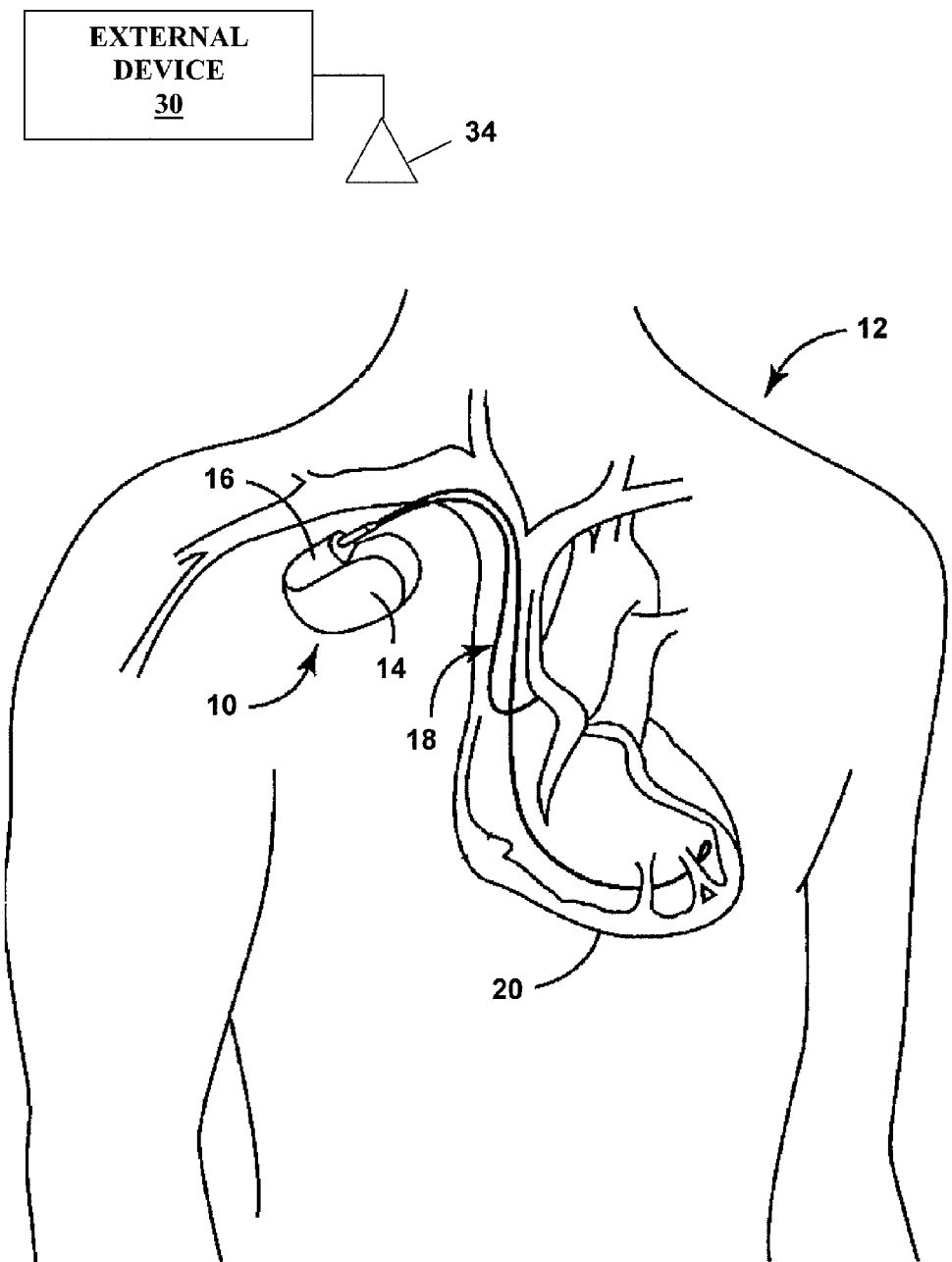
FIG. 1 illustrates an implantable medical device in accordance with an embodiment of the present disclosure implanted in a human body.

The invention provides a method and apparatus for virtually detecting a medical condition in a patient using a set of holistic diagnostic procedures. As described herein, the terms "virtual" and "virtually" shall refer to the use of a monitoring system implemented in a medical device and other components to diagnose medical conditions using automated procedures carried out by means of at least one and preferably a plurality of computing devices. As further described herein, the term "holistic" shall refer to a more all encompassing utilization of sources of complementary diagnostic information to aide in the diagnosis of a medical condition. In one or more embodiments, the system and method are particularly well-suited for detecting acute myocardial infarction (AMI)

in a virtual environment in an accurate and rapid manner shortly after the onset of AMI.

In one or more embodiments, the system and method(s) may be implemented in implantable medical devices (IMDs) that include sensing capabilities for monitoring physiological parameters or conditions and may include therapy delivery capabilities. An IMD in which the invention is implemented may be primarily intended for detecting acute myocardial infarction purposes or may primarily be intended for other purposes. For example, the IMD may comprise any type of implanted device including, but not limited to cardiac pacemakers, implantable cardioverter-defibrillators (ICDs), implantable combination pacemaker-cardioverter-defibrillator (PCDs), implantable brain stimulators, implantable gastric system stimulators, implantable nerve stimulators or muscle stimulators, implantable lower colon stimulators, implantable drug or beneficial agent dispensers or pumps, implantable implantable/insertable subcutaneous ECG event recorders (e.g., such as the MDT Reveal® system, commercially available from Medtronic of Minneapolis, that is capable of automatically detecting and recording a variety of cardiac arrhythmias and manually recording ECG's after symptomatic episodes), or other types of recorders or monitors, proposed implantable gene therapy delivery devices, implantable incontinence prevention or monitoring devices, implantable insulin pumps or monitoring devices, and so on. Reveal is a registered trademark of Medtronic, Inc. of Minneapolis, Minn.

A wide variety of IMDs have been developed to be used as therapeutic devices, where some IMDs further allow for the monitoring of patient conditions and physiological parameters. An IMD typically includes a hermetically sealed housing coupled to one or more leads that are surgically implanted inside a patient for sensing conditions or for administering therapy. The IMD may provide therapeutic stimulation to the patient or may deliver drugs or other beneficial agents to the patient. Alternatively or additionally, the IMD may have sensing or monitoring capabilities. For example, the IMD may sense information within a patient and store the sensed information for subsequent analysis. In some cases, the sensed information may be used directly by the IMD to adjust or control the therapy that is delivered to the patient. Telemetry is used to communicate sensed information from the IMD to an external medical device for further analysis of the sensed information or to initiate further actions. Telemetry is further used to communicate information or instructions from external medical devices to the IMD.

The invention may also be implemented in external medical devices (e.g., 24 to 48 hour hospital-worn Holter-type monitors, external belt-worn ambulatory monitors, etc.) that may be used for monitoring of a patient for virtually detecting a medical condition in a more short-term situation. In the description that follows, various embodiments of the invention are described relating to the detection of AMI. The methods and system provided by the present invention, however, are not limited to the detection of AMI but may be extended to the detection of other types of heart disease or other physiological conditions and diseases, that can be detected by monitoring their respective physiologic indicators, that cause the patients with these conditions and diseases to be at risk for life threatening acute situations, and that require a quick detection and intervention for the best welfare of the patient. This includes patients at risk for acute conditions like syncope, seizures, insulin shock, kidney failure falls, etc.

FIG. 1 is a simplified schematic view of one type of implantable medical device ("IMD") 10 implanted within a human body 12 in which one or more embodiments of the invention may be implemented. IMD 10 comprises a hermetically sealed enclosure 14 and connector module 16 for coupling IMD 10 to electrical leads and other physiological sensors arranged within body 12, such as pacing and sensing leads 18 connected to portions of a heart 20 for delivery of pacing pulses to a patient's heart 20 and sensing of heart 20 conditions. While IMD 10 is depicted in a pacemaker device configuration in FIG. 1, it is understood that IMD 10 may comprise any type of implanted device. IMD 10 collects and processes data from one or more sensors for deriving parameters used in computing a probability that an AMI is occurring in the patient in which IMD 10 is implanted.

Figure 2:
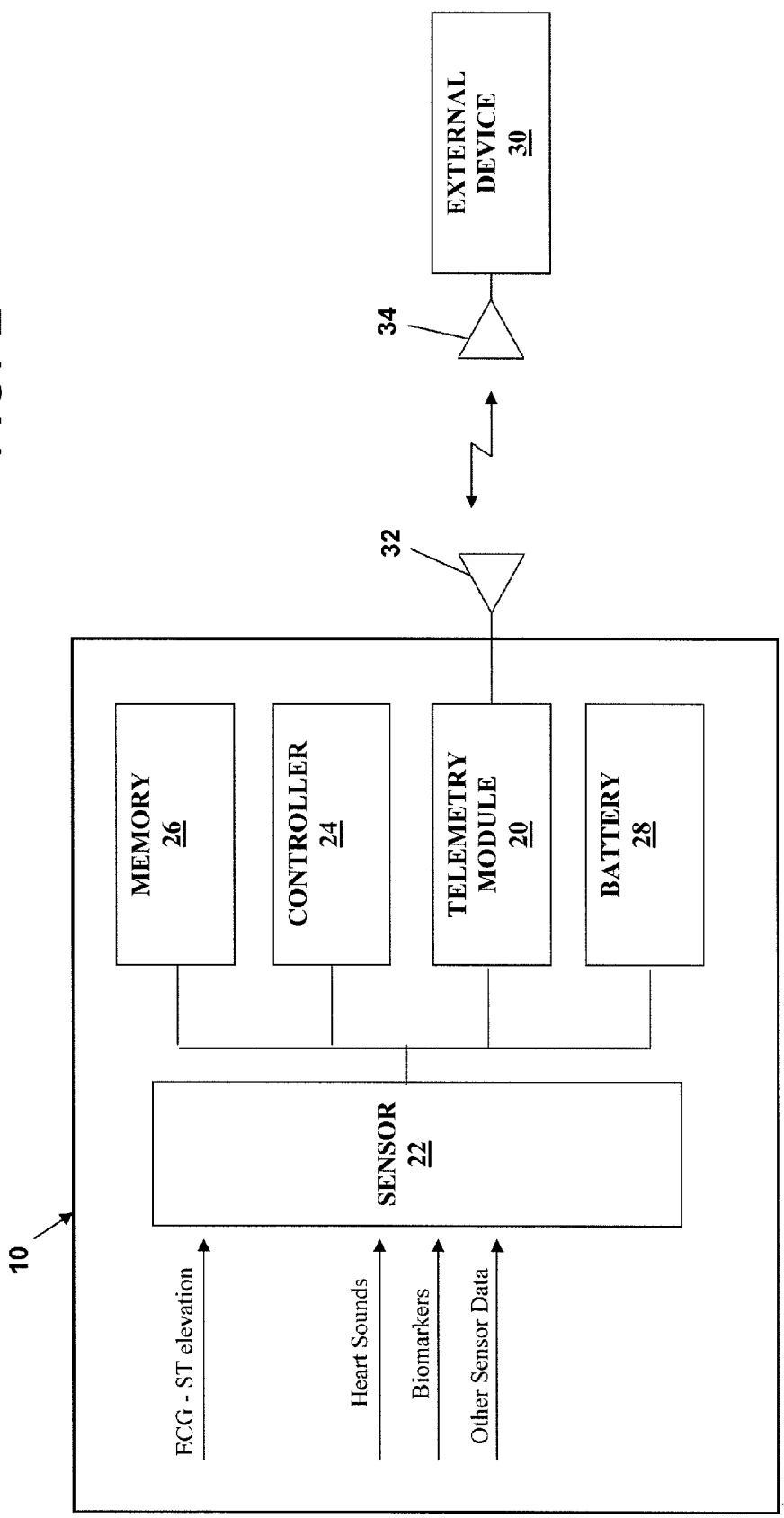
FIG. 2 is a block diagram illustrating the various components of one embodiment of an implantable medical device configured to operate in accordance with the present disclosure.

FIG. 2 is a block diagram illustrating the constituent components of IMD 10 in accordance with one or more embodiments having a microprocessor-based architecture. IMD 10 is shown as including telemetry module 20, at least one sensor 22, processor or controller 24, memory 26, battery 28 and other components as appropriate to produce the desired functionalities of the device.

Controller 24 may be implemented with any type of microprocessor, digital signal processor, application specific integrated circuit (ASIC), field programmable gate array (FPGA) or other integrated or discrete logic circuitry programmed or otherwise configured to provide functionality as described herein. Controller 24 executes instructions stored in memory 26 to provide functionality as described herein. Instructions provided to controller 24 may be executed in any manner, using any data structures, architecture, programming language and/or other techniques. Memory 26 is any storage medium capable of maintaining digital data and instructions provided to controller 24 such as a static or dynamic random access memory (RAM), read-only memory (ROM), non-volatile random access memory (NVRAM), electrically erasable programmable read-only memory (EEPROM), flash memory, or any other electronic, magnetic, optical or other storage medium.

As further shown in FIG. 1, IMD 10 may receive one or more cardiac leads 18 for connection to circuitry enclosed within the housing 14. In one or more embodiments, IMD 10 collects electrogram (EGM) signals or electrocardiogram (ECG) information (e.g., from one or more signals coming from one or more leads, such that the EGM/ECG information may be collected below or above the skin) for use in deriving one or more heart rate related parameters, such as ST segment deviations from normal, desired or expected characteristics or other parameters for use in detecting AMI, as known to those skilled in the art. Other auxiliary leads may further be connected to both IMD 10 and the patient's body for detecting other physiological conditions. Cardiac leads 18 may include, for example, pacing electrodes and defibrillation coil electrodes (not shown) in the event IMD 10 is configured to provide pacing, cardioversion and/or defibrillation. In addition, cardiac leads 18 may deliver pacing stimuli in a coordinated fashion to provide pacing pulses, cardiac resynchronization, extra systolic stimulation therapy or other benefits.

In operation, IMD 10 obtains data via electrodes and/or sensors 22 deployed on leads 18 and/or other sources. This data is provided to controller 24, which suitably analyzes the data, stores appropriate data in memory 26, and/or initiates certain actions as described herein. Any monitored physiological parameters that indicate a likelihood of the occurrence of AMI in the patient can lead to further investigation by IMD 10 or can cause the generation of an alert to the patient, a physician, a caregiver or emergency treatment personnel (e.g., a 911 call). IMD 10 is communicatively coupled to an external device 30 adapted to communicate with IMD 10 and respond to instructions received from IMD 10 or another device.

Communication between IMD 10 and another device can occur via telemetry, such as a long-distance telemetry system through the telemetry module 20. Telemetry module 20 may comprise any unit capable of facilitating wireless data transfer between IMD 10 and an external device 30, where external device 30 may comprise an external medical device, a programming device, a remote telemetry station, a physician-activated device, a patient-activated device, a mobile handheld unit (e.g., mobile phone, PDA, etc.), a personal computer, a patient-wearable device or device capable of being carried by the patient, a display device or any other type of device capable of sending and receiving signals to and from IMD 10. In one or more embodiments, external device 30 may comprise an in-home monitoring device, such as the Medtronic CareLink® Network monitor, that collects information from IMDs implanted in patients and communicates such information to remote clinicians through the Internet, phone lines or wireless networks. Carelink is a registered trademark of Medtronic, Inc. of Minneapolis, Minn. In one or more embodiments, external device 30 may comprise a personal computer, mobile phone or PDA having a software program installed thereon configured for receiving data from IMD 10, processing such data and/or further communicating such data and other information back to IMD 10 and to remote locations.

Telemetry module 20 and external device 30 are respectively coupled to antennas 32 and 34 for facilitating the wireless data transfer. Telemetry module 20 may be configured to perform any type of wireless communication. For example, telemetry module 20 may send and receive radio frequency (RF) signals, infrared (IR) frequency signals, or other electromagnetic signals. In the case of electromagnetic signals, antennas 32 and 34 may comprise coils for transmitting and receiving signals when positioned adjacent to one another. Any of a variety of modulation techniques may be used to modulate data on a respective electromagnetic carrier wave. Alternatively, telemetry module 20 may use sound waves for communicating data, or may use the patient's tissue as the transmission medium for communicating with a programmer positioned on the patients skin. In any event, telemetry module 20 facilitates wireless data transfer between IMD 10 and external device 30. Other types of wired communications may also occur when IMD 10 is alternatively configured as an external medical device or contains wired communication channels that extend from within the patient to points outside of the patient.

IMD 10 includes at least one sensor 22 configured to sense at least one physiological signal or condition, from which a physiological parameter can be monitored. Sensors 22 can monitor electrical, mechanical, chemical, or optical information that contains physiological data of the patient and can utilize any source of physiological signals used for detecting AMI or any other physiological event or condition. In one or more embodiments, sensor 22 is configured to collect electrogram (EGM) signals for use in monitoring ST segment deviations from normal, desired or expected ST segment characteristics. In other embodiments, any potentially ischemic ECG/EGM change can be detected by IMD 10. For example, sensor 22 may comprise a heart sensor, such as the MDT Reveal® system.

In one or more embodiments, sensor 22 is configured to measure heart sounds in the patient, such as S3 and S4 heart sounds. In one or more embodiments, sensor 22 is configured biomarkers that can indicate the onset of a medical condition, such as abnormal levels of concentrations of the enzyme creatine kinase (CK). In one or more embodiments, sensor 22 is configured to sense other physiological conditions useful in detecting AMI or other heart diseases or conditions.

Figure 3:
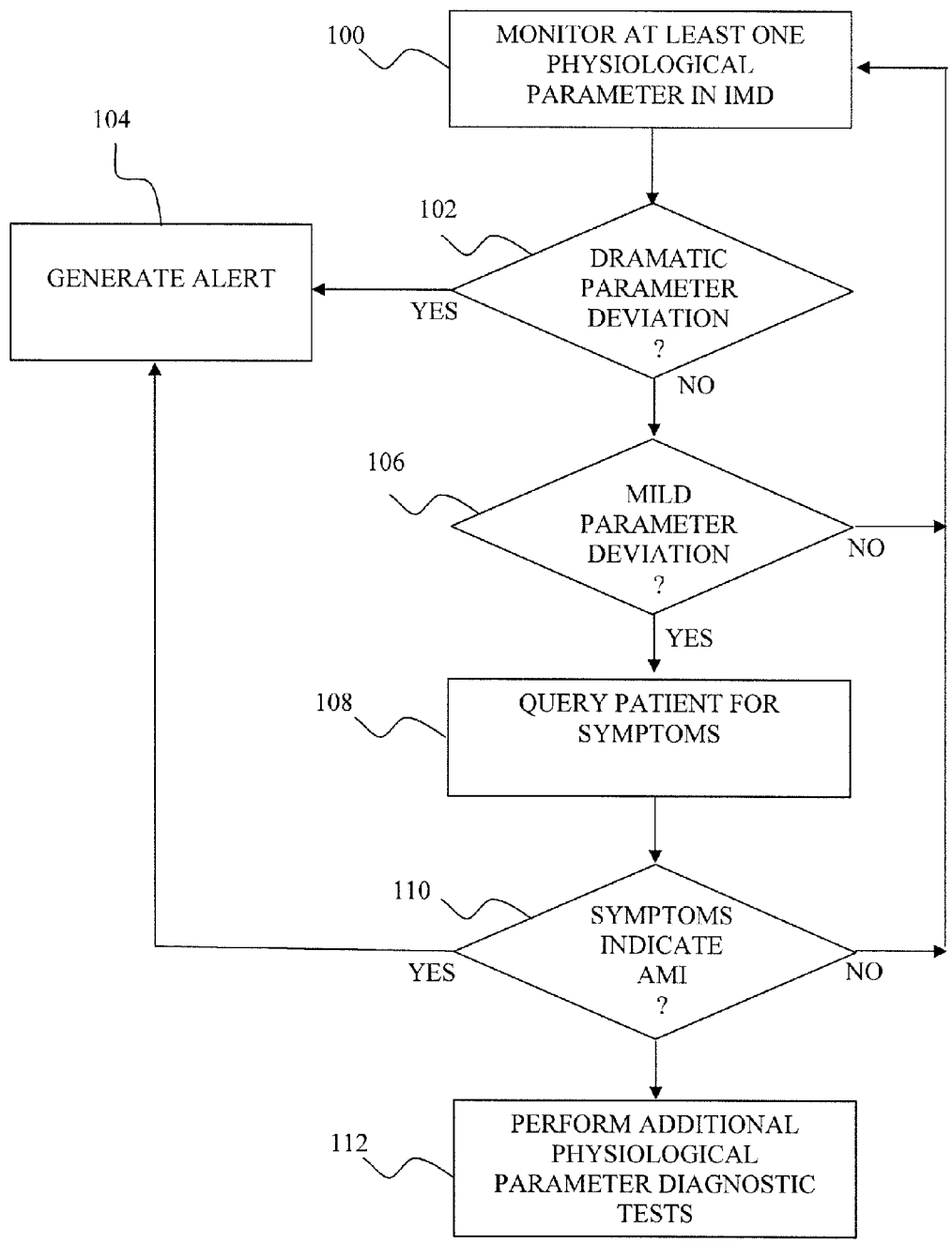
FIG. 3 is an operational flow diagram illustrating a process for virtually detecting a medical condition in accordance with one or more embodiments of the present disclosure.

Referring now to FIG. 3, an operation flow diagram is provided for one or more embodiments of a method for virtually detecting a medical condition occurring in a patient, such as AMI. Medical condition monitoring according to the method of FIG. 3 may be performed continuously, or on a scheduled or triggered basis. For example, IMD 10 may be programmed to operate continuously, during certain hours or additionally or alternatively be enabled to be performed upon a triggering condition. A triggering condition may be an AMI indicator based on an activity signal or other physiological signal or any combination thereof. The triggering condition may also be a request received from the patient, a caregiver, a physician or another individual to initiate diagnostic procedures. For example, when a patient is experiencing certain symptoms and wants to investigate whether such symptoms are related to a certain medical condition, the patient can provide a request or instructions for the diagnostic procedures described herein to be initiated to assist in diagnosing or ruling out whether the patient is experiencing a medical condition.

The method involves sensing at least one physiological signal in the patient's body received in IMD 10 and monitoring a corresponding physiological parameter from each sensed signal in operation 100 to detect deviations in the monitored physiological parameter from normal, desired or expected characteristics. When physiological parameter deviations exist, it is determined in operation 102 whether deviations present in the monitored physiological parameter are sufficient or severe enough so as to indicate with a desired level of certainty that the patient is experiencing a certain medical condition (e.g., AMI). If such a desired level of certainty that the patient is experiencing the medical condition exists, an alert is generated in operation 104 providing notification of the detected condition. In one or more embodiments, the alert may include a patient, physician, caregiver (e.g., nursing home aide, family member, neighbor, etc.) or emergency response (ER) team notification of the detected medical condition, which may further include the transfer of data (e.g., the monitored physiological parameters prompting the alert) from the implantable medical device via a communication link or network. In one embodiment, at least one ECG/EGM signal is initially monitored to detect ST segment deviations or other potentially ischemic ECG/EGM changes that can be an indication that the patient is experiencing an AMI.

In one or more embodiments, if severe deviations in the monitored physiological parameter are not present, it is further determined in operation 106 whether mild or minor (yet possibly suspicious) deviations from desired or expected characteristics are identified to exist in the monitored physiological parameter, where such minor deviations are not severe enough to indicate with a desired level of certainty that the patient is experiencing a certain medical condition. If neither minor nor severe deviations in the monitored physiological parameter are found, then normal physiological parameter monitoring continues in operation 100. If minor deviations in the monitored physiological parameter are found, then additional holistic diagnostic procedures are performed for diagnosing whether the patient is likely to be experiencing the medical condition. In one or more embodiments, the additional holistic diagnostic procedures include querying the patient with questions relating to any symptoms the patient may be experiencing in operation 108. The patient's responses to the symptom-related questions are collected and analyzed in operation 110 further in view of the detected minor physiological parameter deviations to holistically diagnose whether the patient is experiencing a certain medical condition. An alert may be generated in operation 104 when the analysis of the patient's responses to the symptom-related questions indicates with a desired probability that the patient is experiencing the medical condition. In one or more embodiments, when the responses to the patient query fail to indicate with the desired probability that the patient is experiencing the medical condition, the method may perform at least one additional physiological parameter diagnostic test in operation 112 to determine whether the patient is experiencing the medical condition.

Figure 4:
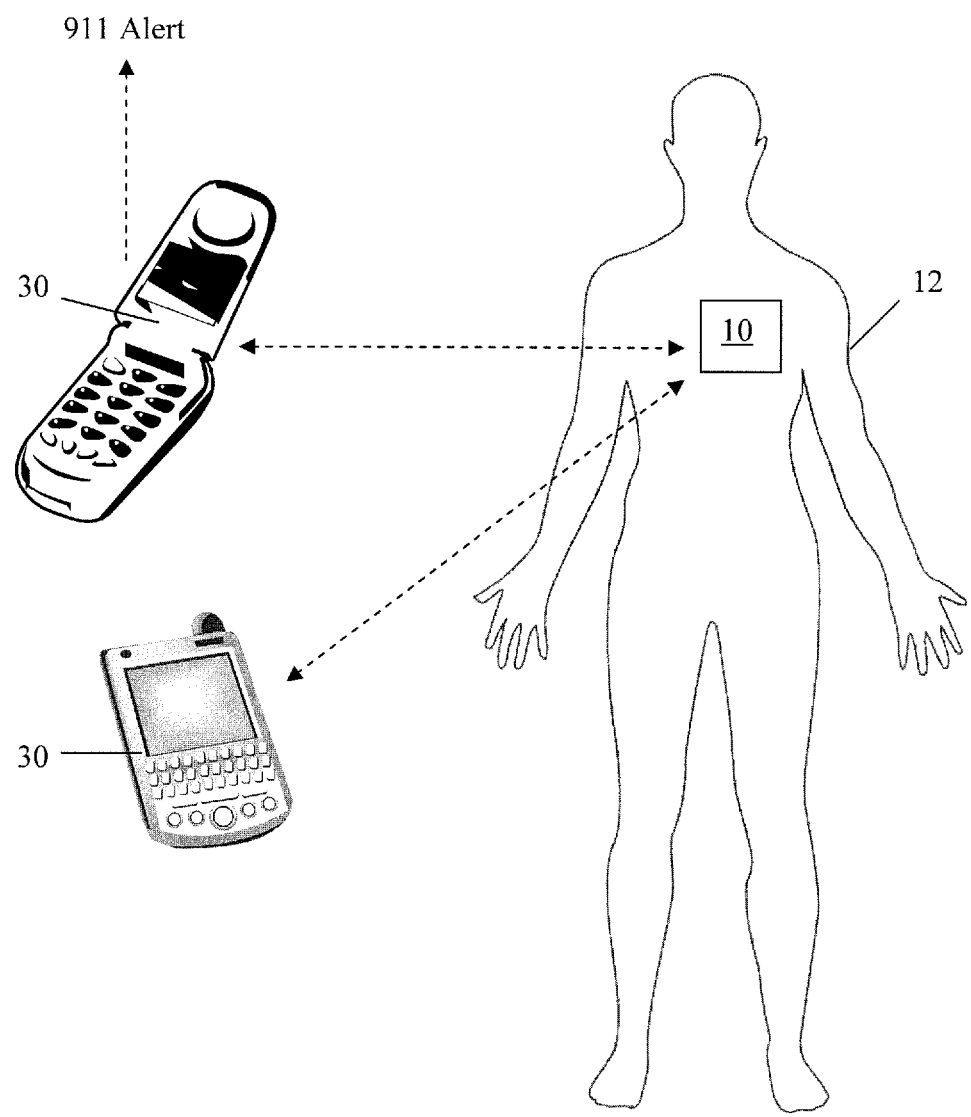
FIG. 4 is a block diagram illustrating various types of external devices capable of communicating with an implantable medical device in accordance with one or more embodiments of the present disclosure.

In one or more embodiments, IMD 10 communicates with external device 30 in order to prompt the patient to answer the symptom-related questions. In one or more embodiments, external device may comprise a mobile phone or PDA, as illustrated in FIG. 4, having customized software and communication components installed thereon to allow such types of external device 30 to communicate with IMD 10. In some embodiments, external device 30 may comprise a portable device capable of being carried by the patient. The external device 30 interacts with the patient in order to mimic the holistic process a physician would follow in order to diagnose acute myocardial infarction. Upon receiving a command or instruction from IMD 10 to query the patient, external device 30 may prompt the patient with a patient questionnaire to be presented to the patient for the patient to provide responses to questions that may help determine whether the medical condition being experienced by the patient. In the case of diagnosing AMI, the patient is queried whether he or she is experiencing certain symptoms associated with AMI, such as typical ischemic chest pain. For example, the patient may be provided with the following questions:

1. Are you feeling chest pain?
2. Is this pain more severe or longer than your previous chest pain?
3. Have you taken nitroglycerin and is your pain relieved?
4. Are you feeling pressure or squeezing in your chest?
5. Are you currently experiencing a cold sweat?
6. Do you currently have nausea?
7. Do you feel short of breath?

These and additional questions can be assigned different weights and asked in a specific order or any order. Once the patient has provided responses to the questions, the likelihood of an AMI event can be determined by the external device 30.

In one or more embodiments, if the patient does not respond within a certain period of time, this lack of responsiveness may be used as an additional factor in determining whether the patient is experiencing a medical condition (i.e., the lack of responsiveness may indicate that the patient is unable to respond based upon the medical condition). External device 30 may thus be configured to determine the amount of time that has elapsed during which external device 30 is waiting for a response from the patient to at least one of the symptom-related questions. In one or more embodiments, additional factors may be analyzed and utilized in determining whether the patient's lack of responsiveness should be given a higher or lower weight when determining whether the patient is experiencing the medical condition, where such factors may include the time of day, the degree of patient activity, or the factors in the patient's surrounding environment. For example, the patient's lack of responsiveness may be due to the patient being asleep (e.g., by sensing the time of day and/or using activity level measurements from accelerometers), due to the patient being involved in a distracting activity (e.g., by using activity level measurements from accelerometers), or due to the patient not being able to sense the prompts to the symptom-related questions (e.g., by sensing acoustic levels in the patient's environment that may prevent the patient from hearing audible alerts). In some embodiments, the position of the patient can be sensed and this position can be used to assist in determining whether the patient is experiencing the medical condition.

Figure 5:
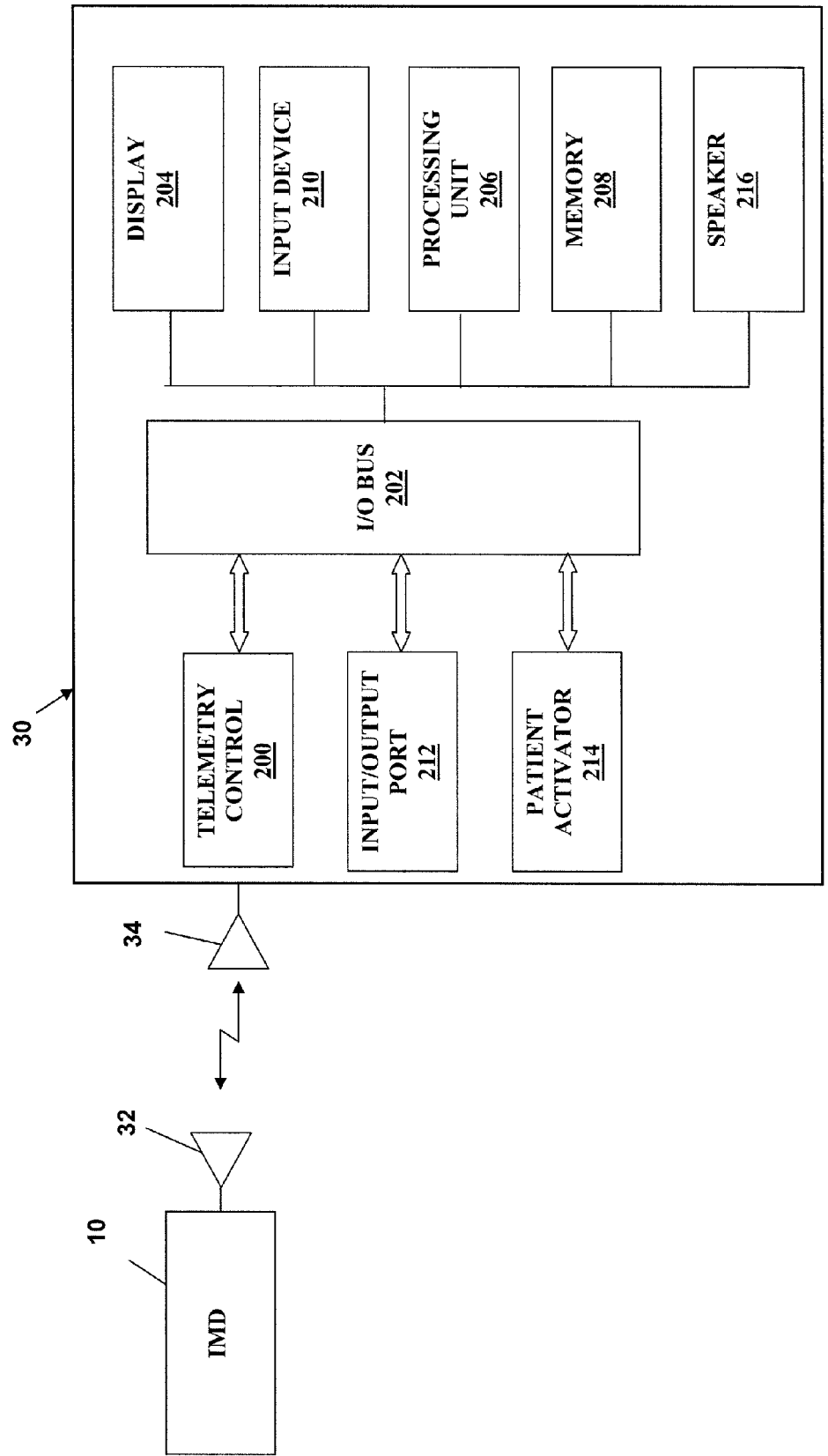
FIG. 5 is a block diagram illustrating the various components of one embodiment of an external device configured to operate in accordance with the present disclosure.

In one or more embodiments, external device 30 includes processing circuitry for interpreting data received from IMD 10 and presenting the questionnaire to the patient on a display of external device 30 or another device. Referring now to FIG. 5, a block schematic illustration of external device 30 is provided in accordance with one or more embodiments. External device 30 includes an antenna 34, coil or wired input for communicating data and other signals between external device 30 and IMD 10. Data and instructions are received from IMD 10 through antenna 34, which is connected to telemetry/antenna control circuit or module 200 that serves to demodulate telemetry signals received through antenna 34. The demodulated signals are applied in parallel or serial digital format to input/output (I/O) unit or bus 202, where they in turn may be applied to a display or screen 204, output through speaker 216, provided to processing unit 206 and/or memory 208. Processing unit 206 includes any type of microprocessor, digital signal processor, application specific integrated circuit (ASIC), field programmable gate array (FPGA) or other integrated or discrete logic circuitry programmed or otherwise configured to control operating of the external device 30 and provide functionality as described herein. In one embodiment, processing unit 206 executes instructions associated with a software program or module stored in memory 208 to provide functionality as described herein.

In one or more embodiments, external device 30 includes an input device 210 that allows data, commands or selections to be input into the external device 30 by a patient, physician or clinician. Input device 210 may include, but is not limited to, at least one of the following: a keyboard, track ball, mouse, touch-sensitive displays, push buttons, magnetic readers, RF readers, tablets, styluses, microphones, voice recognizers, handwriting recognizers and any other device that allows a patient, physician or clinician to input data to external device. Processing unit 206 controls operation of display 204 and is responsive to commands received from input device 210. Memory 208 is suitable for storing data received from IMD 10, input device 210, processing unit 206 or other data or commands otherwise received by external device 30. External device may further include an input/output port 212 for connecting external device 30 to other devices, communication networks, phone lines, wireless devices, etc. In one or more embodiments, external device 30 may relate information to the patient or a clinician by sound through speakers 216 in addition to or instead of presenting such information on display 204. In some embodiments, external device 30 may provide patient with an indication that prompts the patient to answer the questionnaire, such as a visual indication (indicator light or message on the display screen 204), an audio indication through speakers 216 or a vibrating sensation or other physical notification that the patient can feel.

The information contained in the patient's responses can either be used directly by external device 30 in arriving at a determination that AMI is likely occurring or the information can be transmitted back to IMD 10 for further processing or to a remote location (e.g., a server at the physician's office, hospital or another clinical location) for further virtual processing and analysis. An alert may be generated when the analysis of the patient's responses to the symptom-related questions indicates with a desired probability that the patient is experiencing the medical condition.

In one or more embodiments, the possible alerts may include a notification to the patient (e.g., through the display 204 or speakers 216 of external device 30) or a transmitted alert to a physician, hospital or emergency response (ER) team. In some embodiments, the alert may include generating instructions to the patient, a physician, a clinician or an ER individual to take certain actions for treating the diagnosed condition. For example, the patient can be alerted of the diagnosed medical condition and notified with instructions to take certain therapeutic actions (e.g., taking aspirin, nitrates, fluids, pain killers, diuretics, thrombolytic agents, etc. or possibly instructions that the patient should immediately go to the emergency room or other types of actions). In some embodiments, external device 30 or another medical device may be equipped with the therapeutic materials the patient is instructed to use. Still further, the instructions can instruct the patient, emergency response personnel and/or bystanders to take appropriate actions to treat the detected condition, where such instructions could be part of a bi-directional communication that occurs with paramedics/physicians that were alerted of the detected condition. In some embodiments, the possible automated responses include providing instructions for collecting additional physiological parameter data, where this additional information can be used to further diagnose additional aspects of the medical condition. In some embodiments, the alert may provide IMD 10 or another medical device with instructions for causing certain therapeutic actions to be performed on the patient (e.g., causing overpacing of the patient's heart to increase blood flow, delivering nitroglycerin, etc.).

In one or more embodiments, when the responses to the patient query fail to indicate with the desired probability that the patient is experiencing the medical condition, external device 30 is further configured for causing at least one additional physiological parameter diagnostic test to be performed to determine whether the patient is experiencing the medical condition. In some embodiments, the additional physiological parameter diagnostic tests are performed automatically by instructing IMD 10 or another device to obtain measurements of another physiological parameter. In some embodiments, the patient is instructed by external device 30 to perform the additional physiological parameter diagnostic tests and either the patient could be asked to enter the results of such tests into external device 30 for further diagnostic analysis or the external devices used in performing these additional diagnostic tests could transmit the data directly a component of the system for further diagnostic analysis.

In one or more embodiments, if the diagnosis realized at any of the various stages of the diagnostic procedures is negative, the patient may be notified of the negative diagnosis. The notification of the negative diagnosis (e.g., notification that the patient is not experiencing a certain medical condition) adds to the effective result of the holistic diagnosis that is performed virtually. For example, when a patient has conventionally visited a physician because the patient is experiencing certain symptoms, the patient wants and expects the physician to rule out that the patient is experiencing a certain medical condition. Thus, by further providing the patient with a negative diagnosis, the system and method provide a virtual method for comforting the patient with an understanding any symptoms the patient is experiencing are unrelated to a certain medical condition. One problem often hindering the ability for physicians to detect medical conditions in patients in a timely-manner is the reluctance for patients to seek medical attention each and every time they experience a symptom. Often times, patients will wait until their symptoms are severe before they seek medical attention. By using the systems and methods set forth in one or more of the embodiments described herein for virtually detecting a medical condition in a patient using holistic diagnostic procedures, patients may initiate the diagnostic procedures on their own accord to determine whether symptoms they are experiencing are related to medical conditions without having to seek physician assistance. Further, in one or more embodiments, there is no limit to the number of times that a patient may request the virtual diagnostic procedures to be performed, which may lead a patient to request the diagnostic procedures to be performed often, hopefully leading to an early detection or indication of a medical condition for which the patient can then seek medical treatment. A patient may feel more comfortable simply initiating the virtual diagnostic procedures to help diagnose or rule out that certain symptoms are related to a medical condition than seeking out physician assistance. If the patient receives an indication of a negative diagnosis, this may prevent the patient from unnecessarily contacting a physician to merely arrive at the same conclusion. Many of the same holistic diagnostic procedures typically followed by physicians can thus be performed virtually. In some embodiments, physician assistance can be reserved to those instances when it is actually required instead of the 'false alarms' that a patient wants to have checked out.

Figure 6:
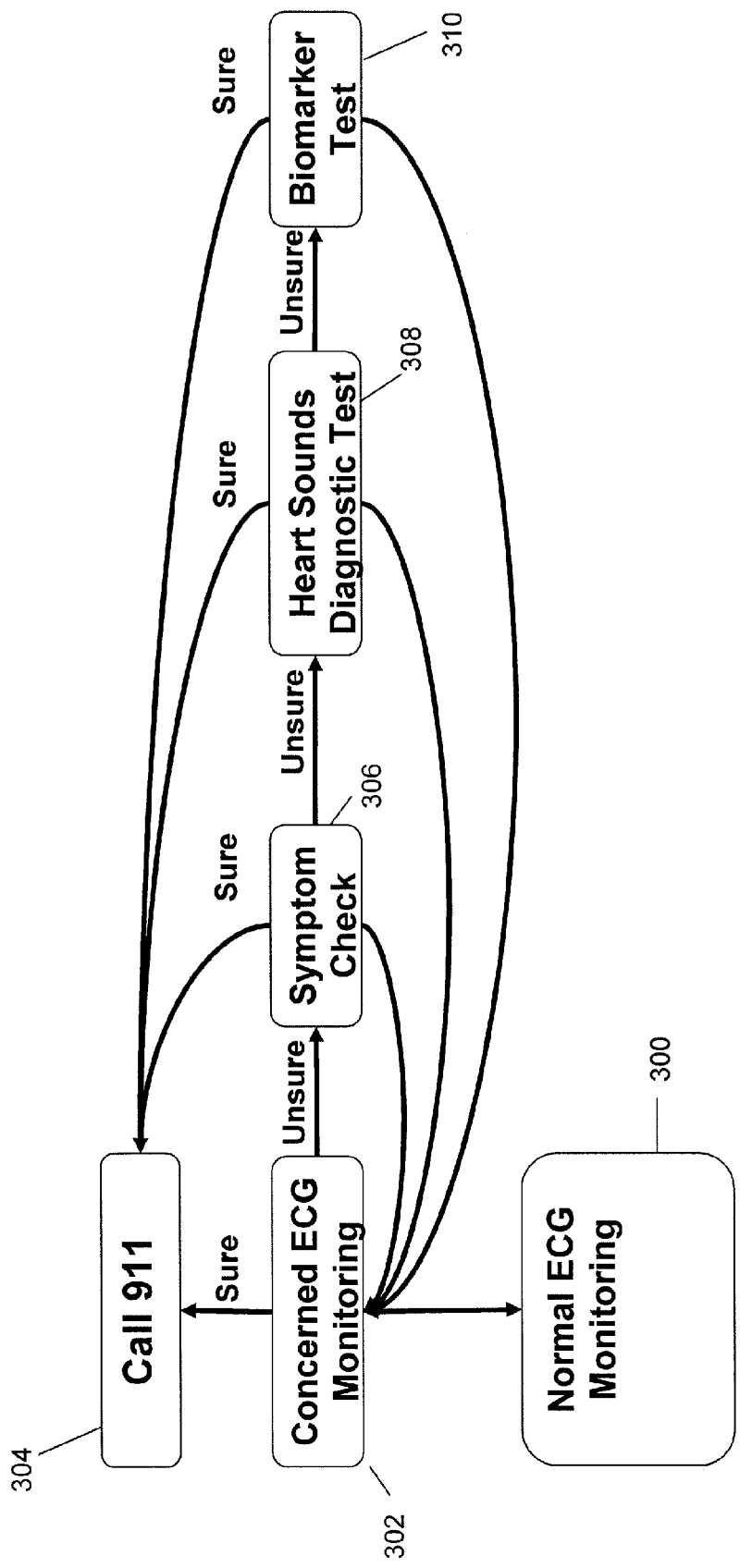
FIG. 6 is a state diagram illustrating various stages and states of the virtual holistic diagnostic procedures in accordance with one or more embodiments of the present disclosure.

Referring now to FIG. 6, a block diagram state diagram is illustrated for various stages and states of the virtual holistic diagnostic system and method including the additional physiological parameter diagnostic tests for one or more embodiments in which AMI is detected. The system is in a Normal Monitoring state 300 when the monitored physical parameter (i.e., the ST segment deviations in the EGM signal) indicates that no minor or severe deviations exist. A Concerned EGM Monitoring state 302 is entered into if any deviations exist in the monitored physical parameter from normal, expected or desired characteristics. In some embodiments, if severe deviations in the monitored physical parameter exist, an Emergency state 304 is entered into in which emergency response personnel or the patient can be notified (e.g., call 911). If minor deviations in the monitored physical parameter from the Concerned EGM Monitoring State 302, a Symptom Check state 306 is entered into in which the patient is prompted to answer the symptom-related query as described herein. The Emergency state 304 is entered into if the information contained in the patient's responses leads to a determination that AMI is likely occurring in the patient.

If the diagnosis is unsure after the Symptom Check state 306, additional physiological parameter diagnostic tests can be performed in any order. In some embodiments, the additional physiological parameter diagnostic tests are performed automatically by instructing IMD 10 or another device to obtain measurements of another physiological parameter. In some embodiments, the patient is instructed to perform the additional physiological parameter diagnostic tests and enter the results of such tests into external device 30. Either IMD 10 or external device 30 or the combination of both may then process and analyze the data from the additional physiological parameter diagnostic tests to determine whether AMI is occurring in the patient. In some embodiments, a Heart Sounds Diagnostic Test state 308 is entered into in which IMD 10 monitors the patient's heart sounds.

There are four audible heart sounds which may be present during each heartbeat that may be used to augment the diagnosis of heart conditions, where not all of the four heart sounds are always present. These heart sounds are generally considered to be produced by blood turbulence and vibration of cardiac structures due primarily to the closing of the valves within the heart. The four heart sounds are referred to as S1, S2, S3, and S4. The first heart sound, S1, is usually the loudest heart sound and occurs during the start of ventricular contraction or systole. S1 has been shown to relate to the closure of the atrioventricular valves between the atria and the ventricles. The second heart sound, S2, occurs at the beginning of diastole and has been shown to relate to the closing of the semilunar valves separating the aorta and pulmonary artery from the left and right ventricles, respectively. The third heart sound, S3, can occur in the early diastolic period and is considered to be caused by the ventricular wall distending to the point that it reaches its elastic limit. The fourth heart sound, S4, can occur near the end of atrial contraction and is also considered to be caused by the ventricular wall distending to the point that it reaches its elastic limit. The S1 and S2 heart sounds are always present in normal function of the heart and the S3 and S4 are generally only seen in normal function of the heart in young people or in some highly trained athletes, otherwise they are generally considered to be indicative of abnormal heart function, and may be present in people suffering from heart failure or ischemia.

These monitored sounds can be useful in making a more accurate MI diagnosis. In some embodiments, the Heart Sounds Diagnostic Test state 308 monitors the S3 and S4 heart sounds for signs of ischemia. In some embodiments, external device 10 can provide the patient with an alert or instructions to get into a particular posture, such as laying on their back, in order to eliminate movement noise that could interfere with accurate heart sound readings. Once the patient is positioned into the desired position, as may be confirmed by an additional posture monitoring sensor such as a 3-axis accelerometer, IMD 10 can listen for the S3 and S4 heart sounds with the body in a quiet, known position. If it is determined that the patient has not assumed the desired posture, a reminder could be sent to the patient In some embodiments, noise and other interference that could degrade the quality of the physiological signals monitored by IMD 10 can be monitored. If IMD 10 detects an AMI based on physiological signals received by sensor 22 but an EGM noise detector circuit or high activity detector circuit via an accelerometer indicates that the physiological signals received by sensor 22 are unreliable due to noise or other possible interferences, the virtual physician system can prompt the patient with an alert or instructions to stop movement and/or get into a particular posture to eliminate movement noise that could interfere with accurate sensor readings. In some embodiments, the system could then verify through posture measurements and activity levels that the orders have been followed the patient, and new measurements can then be taken when it is determined that the patient complied with such instructions.

If the diagnosis is unclear after the Heart Sounds Diagnostic Test state 308, a Biomarker Test state 310 can be entered into in which biomarkers in the patient's blood can be monitored to detect raised concentrations of certain biomarkers that provide an indication of a medical condition, such as raised concentrations of the enzyme creatine kinase (CK) in blood to detect AMI. Biomarkers are used in this model as a last resort due to the number of hours typically required before detectable levels of these biomarkers are present in the blood. However, a rise in the myocardial band (MB) of creatine phosphokinase (CPK) to abnormal levels is an almost 100% specific identifier for myocardial infarction. If biomarkers in the Biomarker Test state 310 indicate that a cardiac infarction has occurred, the Emergency state 304 should be entered and the patient should further be instructed to be admitted to the hospital for further care and testing. In one or more embodiments, IMD 10 could autonomously conduct a biomarker test (e.g., an enzyme test). In another embodiment, external device 30 could instruct the patient to take a biomarker test (e.g., such as an enzyme test that is similar to a home pregnancy test or glucose test) in which the patient can test himself and then input the results into the external device 30.

Figure 7:
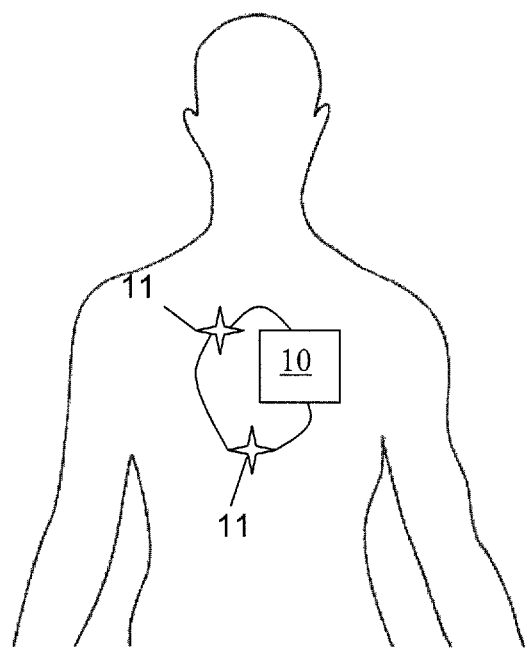
FIG. 7 illustrates a plurality of distributed devices implanted in a human body in accordance with an embodiment of the present disclosure.

In one or more embodiments, the physical location of the AMI within the heart determines the ideal position of IMD 10 to sense the ST segment deviation. In some embodiments, multiple devices 11 that communicate with each other and/or IMD 10 could be used to look for abnormal ST segment deviations, as illustrated in FIG. 7. In some embodiments, the devices 11 communicate either actively or passively with IMD 10 that serves as a central communication device or the central communication device may be located external to the patient. In some embodiments, multiple devices 10 and 11 are used to look for abnormal ST segment deviations that each function independently. As such, if any one of the devices 10 or 11 sense abnormal ST segment deviations, the device that senses the abnormal event will initiate the next actions as described herein.

In one or more embodiments, the system and method may further allow the patients themselves to initiate various diagnostic procedures to be performed and analyzed virtually, e.g., the Biomarker test. At a point in time when a patient is experiencing a physiological symptom that the patient is concerned could be associated with a certain medical condition, the patient could initiate a program operating on external device 30 in which the patient inputs a certain symptom the patient is experiencing or the patient otherwise provides an indication that the patient wants certain diagnostic procedures to be performed. External device 30 then sends instructions to IMD 10 to initiate the diagnostic procedures for virtually detecting whether a patient is experiencing a medical condition as described herein. For example, if a patient is experiencing heartburn and wonders if this physiological sensation is actually a mild heart attack, the patient could request through external device for diagnostic procedures to be implemented to detect if any abnormal physiological parameters are being sensed in the patient (such as abnormal ST deviations). In some embodiments, the patient may be able to activate IMD 10 directly to perform the diagnostic procedures (e.g., using a taptivator sensor, etc.). In embodiments in which the diagnostic procedures are not implemented until when the patient initiates a request for such procedures to be performed, substantial power consumption in IMD 10 can be conserved, thereby improving the battery life of IMD 10.

By utilizing a virtual holistic approach to AMI diagnosis, the present system and method provide a means to achieve higher sensitivity and specificity than is possible using the conventional methods of solely relying on an ECG or EGM. Further, the system and method for detecting AMI and providing a response thereto described in the various embodiments herein allow AMI to be diagnosed in near real-time to when AMI is initially experienced by a patient. This allows therapies and responses to be delivered to the patient without significant delay, thereby adding to likelihood of the effectiveness of the therapy and treatment provided to the patient.

While the system and method have been described in terms of what are presently considered to be specific embodiments, the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A virtual physician system comprising:
a medical device implantable in a patient and configured to monitor at least one physiological parameter from sensed physiological signals for deviations from desired characteristics;
the implantable medical device configured to:
determine whether sufficient deviations are present in the monitored physiological parameter(s) that indicate with a desired level of certainty that the patient is experiencing a certain medical condition;
generate an alert when the desired level of certainty that the patient is experiencing the medical condition is determined to exist;
determine whether minor deviations are present in the monitored physiological parameter that potentially indicate that the patient is experiencing the medical condition without reaching with the desired level of certainty that the patient is experiencing the medical condition, wherein the minor deviations are not sufficient to indicate with the desired level of certainty that the patient is experiencing the certain medical condition;
cause additional holistic diagnostic procedures to be performed for diagnosing whether the patient is experiencing the medical condition when minor deviations are determined;
cause, as at least part of the additional holistic diagnostic procedures, an external device to query the patient regarding symptom-related questions and collect responses to the symptom-related questions from the patient; and
cause, when the minor deviations are determined to be present, a determination of whether the patient is experiencing the medical condition based on the presence of the minor deviations and the collected responses to the symptom-related questions from the patient.

2. The virtual physician system of claim 1, further comprising the external device, wherein the external device is configured to communicate with the implantable medical device, the external device including an interface for allowing information to be communicated to and from the patient,
the implantable medical device further configured for transmitting a command to the external device to query the patient regarding symptom-related questions.

3. The virtual physician system of claim 2, wherein the external device is further configured to collect responses to the symptom-related questions and analyze the responses to the symptom-related questions in view of the detected minor physiological parameter deviations to diagnose whether the patient is experiencing the medical condition.

4. The virtual physician system of claim 3, wherein, when the symptom-related information collected from the patient fails to indicate with the desired probability that the patient is experiencing the medical condition, the external device is further configured to cause at least one additional physiological parameter diagnostic test to be performed to determine whether the patient is experiencing the medical condition.

5. The virtual physician system of claim 4, wherein the implantable medical device is configured to monitor electrogram (EGM) or electrocardiogram (ECG) information received in the implantable medical device for ST segment deviations and wherein the medical condition to be diagnosed is acute myocardial infarction, further wherein the at least one additional physiological parameter diagnostic test includes at least one of a heart sounds diagnostic test and a biomarker test.

6. The virtual physician system of claim 1, further comprising a plurality of distributed devices arranged with respect to the patient for monitoring the physiological parameter in conjunction with the implantable medical device for deviations from desired characteristics.

7. The virtual physician system of claim 2, wherein the external device is further configured to receive a request for the activation of the implantable medical device to initiate the monitoring of the physiological parameter from sensed physiological signals and to deliver instructions to the implantable medical device to initiate said monitoring.

8. The virtual physician system of claim 2, wherein the external device is further configured to provide instructions for the patient to follow to assist in the performance and reliability of the at least one additional diagnostic test.

9. The virtual physician system of claim 2, wherein the external device is further configured to provide instructions for the patient to perform at least one additional diagnostic test and configured to receive the results of such tests performed from the patient, the results of which are provided by the patient for use in detecting with the desired probability whether the patient is experiencing the medical condition.

10. The virtual physician system of claim 2, wherein the external device is further configured to receive a request from the patient for initiating the procedures for determining whether the patient is experiencing a certain medical condition.

11. The virtual physician system of claim 2, wherein the external device is further configured to provide a notification of a negative diagnosis when it is virtually determined that the patient is not experiencing the medical condition.

12. The virtual physician system of claim 2, further comprising a remote server, wherein the external device is configured to collect responses to the symptom-related questions and transmit the collected responses to the remote server, and wherein the remote server is configured to analyze the responses to the symptom-related questions in view of the detected minor physiological parameter deviations to diagnose whether the patient is experiencing the medical condition.

13. The virtual physician system of claim 1, wherein the implantable medical device is configured to, upon determining that minor deviations are present, cause the additional holistic diagnostic procedures to be performed for diagnosing whether the patient is experiencing the medical condition when minor deviations are determined.

14. The virtual physician system of claim 1, wherein the implantable medical device is configured to determine whether the patient is experiencing the medical condition based on the minor deviations and the collected responses to the system-related questions from the patient.

15. The virtual physician system of claim 1, wherein the external device is configured to determine whether the patient is experiencing the medical condition based on the minor deviations and the collected responses to the system-related questions from the patient.

16. The virtual physician system of claim 3, wherein the external device is configured to:
prompt the patient to respond to the symptom-related questions;
determine when at least one of the responses to the symptom-related questions is not collected within a certain period of time; and
diagnose whether the patient is experiencing the medical condition based, at least in part, on not collecting the at least one response within the certain period of time.

* * * * *